(12) United States Patent
Stetson

(10) Patent No.: US 6,701,170 B2
(45) Date of Patent: Mar. 2, 2004

(54) BLIND SOURCE SEPARATION OF PULSE OXIMETRY SIGNALS

(75) Inventor: Paul F. Stetson, Oakland, CA (US)

(73) Assignee: Nellcor Puritan Bennett Incorporated, Pleasanton, CA (US)

(*) Notice: Subject to any disclaimer, the term of this patent is extended or adjusted under 35 U.S.C. 154(b) by 0 days.

(21) Appl. No.: 10/033,703

(22) Filed: Nov. 2, 2001

(65) Prior Publication Data

US 2003/0088164 A1 May 8, 2003

(51) Int. Cl.$^7$ ................................. A61B 5/00
(52) U.S. Cl. .................. 600/323; 600/324; 600/502
(58) Field of Search .................. 600/309–310, 600/300, 322–326, 709, 481, 500–502

(56) References Cited

U.S. PATENT DOCUMENTS

| | | | |
|---|---|---|---|
| 4,911,167 A | | 3/1990 | Corenman et al. |
| 5,315,532 A | | 5/1994 | Comon |
| 5,337,745 A | | 8/1994 | Benaron |
| 5,349,953 A | | 9/1994 | McCarthy et al. |
| 5,645,059 A | | 7/1997 | Fein et al. |
| 5,706,402 A | * | 1/1998 | Bell ............................ 706/22 |
| 5,853,364 A | | 12/1998 | Baker, Jr. et al. |
| 5,928,146 A | * | 7/1999 | Itagaki et al. ............... 600/410 |
| 6,232,609 B1 | * | 5/2001 | Snyder et al. ............. 250/461.1 |
| 6,424,960 B1 | * | 7/2002 | Lee et al. .................... 600/310 |
| 2002/0069242 A1 | * | 6/2002 | Berns ........................ 709/203 |
| 2002/0085741 A1 | * | 7/2002 | Shimizu ..................... 382/118 |

FOREIGN PATENT DOCUMENTS

WO    WO 00/42911 A1    7/2000

OTHER PUBLICATIONS

Amari et al., A New Learning Algorithm for Blind Signal Separation,*Advances in Neural Information Processing Systems 8*, pp. 757–763 (1996).
Comon, "Independent Component Analysis, a New Concept?" *Signal Processing*, 36(3):287–314 (1994).
De Lathauwer et al., "ICA Techniques for More Sources than Sensors," *Proceedings of the IEEE Signal Processing Workshop on Higher–Order Statistics*, pp. 121–124 (1999).
Makeig et al., "Independent Component Analysis of Electroencephalographic Data," *Advances in Neural Information Processing Systems 8*, pp. 145–151 (1996).
McKeown et al., "Analysis of fMRI Data by Blind Separation Into Independent Spatial Components," *Human Brain Mapping*, 6:160–188 (1998).

* cited by examiner

*Primary Examiner*—Eric F. Winakur
*Assistant Examiner*—Matthew Kremer
(74) *Attorney, Agent, or Firm*—Townsend & Townsend & Crew LLP

(57) ABSTRACT

A method and apparatus for the application of Blind Source Separation (BSS), specifically independent Component Analysis (ICA) to mixture signals obtained by a pulse oximeter sensor. In pulse oximetry, the signals measured at different wavelengths represent the mixture signals, while the plethysmographic signal, motion artifact, respiratory artifact and instrumental noise represent the source components. The BSS is carried out by a two-step method including an ICA. In the first step, the method uses Principal Component Analysis (PCA) as a preprocessing step, and the Principal Components are then used to derive sat and the Independent Components, where the Independent Components are determined in a second step. In one embodiment, the independent components are obtained by high-order decorrelation of the principal components, achieved by maximizing the sum of the squares of the higher-order cumulants of the plurality of mixture signals.

38 Claims, 6 Drawing Sheets

BLIND SOURCE SEPARATION OF PULSE OXIMETRY SIGNALS

BACKGROUND OF THE INVENTION

The present invention relates to the processing of signals obtained from a medical diagnostic apparatus such as a pulse oximeter using a blind source separation technique to separate the obtained data without prior knowledge of its magnitude or frequency into data corresponding to the desired physiological data and the undesired interference sources.

A typical pulse oximeter measures two physiological parameters, percent oxygen saturation of arterial blood hemoglobin ($SpO_2$ or sat) and pulse rate. Oxygen saturation can be estimated using various techniques. In one common technique, the photocurrent generated by the photo-detector is conditioned and processed to determine the ratio of modulation ratios (ratio of ratios) of the red to infrared signals. This modulation ratio has been observed to correlate well to arterial oxygen saturation. The pulse oximeters and sensors are empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. The estimation of oxygen saturation using modulation ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING", issued Dec. 29, 1998, and U.S. Pat. No. 4,911,167, entitled "METHOD AND APPARATUS FOR DETECTING OPTICAL PULSES", issued Mar. 27, 1990. The relationship between oxygen saturation and modulation ratio is further described in U.S. Pat. No. 5,645,059, entitled "MEDICAL SENSOR WITH MODULATED ENCODING SCHEME," issued Jul. 8, 1997. Most pulse oximeters extract the plethysmographic signal having first determined saturation or pulse rate, both of which are susceptible to interference.

A challenge in pulse oximetry is in analyzing the data to obtain a reliable measure of a physiologic parameter in the presence of large interference sources. Prior art solutions to this challenge have included methods that assess the quality of the measured data and determine to display the measured value when it is deemed reliable based upon a signal quality. Another approach involves a heuristic-based signal extraction technology, where the obtained signals are processed based on a series of guesses of the ratio, and which require the algorithm to start with a guess of the ratio, which is an unknown. Both the signal-quality determining and the heuristic signal extraction technologies are attempts at separating out a reliable signal from an unreliable one, one method being a phenomenological one and the other being a heuristic one.

On the other hand, a problem encountered in such disciplines as statistics, data analysis, signal processing, and neural network research, is finding a suitable representation of multivariate data. One such suite of methods is generally known as Independent Component Analysis (ICA), which is an approach to the problem of Blind Source Separation (BSS).

In general terms, the goal of blind source separation in signal processing is to recover independent source signals after they are linearly mixed by an unknown medium, and recorded or measured at N sensors. The blind source separation has been studied by researchers in speech processing or voice processing; antenna array processing; neural network and statistical signal processing communities (e.g. P. Comon, "Independent Component Analysis, a New Concept?", Signal Processing, vol. 36. no. 3, (April 1994), pp. 287–314, "Comon") and applied with relative degrees of success to electroencephalogram data and functional MRI imaging.

Comon defined the concept of independent component analysis as maximizing the degree of statistical independence among outputs using "contrast" functions of higher-order cumulants. Higher-order statistics refer to the expectations of products of three or more signals (e.g. $3^{rd}$-order or $4^{th}$-order moments), and cumulants are functions of the moments which are useful in relating the statistics to those of the Gaussian distribution. The $3^{rd}$-order cumulant of a distribution is called a skew, and the $4^{th}$-order cumulant is the kurtosis. A contrast function is any non-linear function which is invariant to permutation and scaling matrices, and attains its minimum value in correspondence of the mutual independence among the output components. In contrast with decorrelation techniques such as Principal Component Analysis (PCA), which ensures that output pairs are uncorrelated, ICA imposes the much stronger criterion that the multivariate probability density function of output variables factorizes. Finding such a factorization requires that the mutual information between all variable pairs go to zero. Mutual information depends on all higher-order statistics of the output variables while decorrelation normally only takes account of 2nd-order statistics.

While the general use of ICA as a means of blindly separating independent signal sources is known, the method poses unique challenges to its implementation in pulse oximetry. For instance, the mixture signals may not be exactly a linear combination of the pulse signal and sources of interference. Also, most ICA techniques are based on fourth-order cumulants, as the signals and noise commonly encountered in communications have zero third-order cumulant (skew), and cumulants of higher than fourth order are difficult to estimate accurately.

Several ICA methods are known for separating unknown source signals from sets of mixture signals, where the mixture signals are a linear combination of the source signals. As used in pulse oximetry, the mixture signals refer to signals measured at multiple wavelengths. Source components refer to the desired physiologic data including signals corresponding to the plethysmographic signal obtained at multiple wavelengths in addition to undesired interference data, which may be caused by motion, light interference, respiratory artifacts, and other known sources of errors in pulse oximetry.

There is therefore a need to apply blind source separation techniques to the field of pulse oximetry to be able to deterministically separate a source signal from various interference sources.

BRIEF SUMMARY OF THE INVENTION

The present invention is directed towards a method and apparatus for the application of Blind Source Separation (BSS), specifically Independent Component Analysis (ICA) to pulse oximetry. ICA refers to any one of several methods for separating unknown source signals from a set of "mixture" signals, which are linear combinations of the source signals. These methods may use estimates of the second- and higher-order joint statistics of the mixture signals and separate the sources by seeking to minimize the mutual information of the outputs of separation. In pulse oximetry, the signals measured at different wavelengths represent the mixture signals, while the plethysmographic signal, motion artifact, respiratory artifact and instrumental noise represent the source components.

In one embodiment the BSS is carried out by a two-step method including PCA and a higher-order decorrelation. In the first step, the method uses PCA as a preprocessing step, and in a second step, the principal components are then used to derive the independent components and the desired physiological parameters. The PCA is performed to transform the data to have zero second-order correlation before higher-order decorrelation.

In one aspect of the method of the present invention, data corresponding to a plurality of signals measured at a plurality of wavelengths are first obtained. Next, the data are processed to obtain a plurality of principal components, where in one embodiment the principal components are obtained by decorrelating the data (to minimize the cross-correlation between the signals from different wavelengths), and normalizing the decorrelated data. Next, the principal components are processed to obtain a plurality of independent components, wherein a matrix of the plurality of signals corresponds with a matrix product of a matrix of the plurality of independent components and a matrix of mixing coefficients. In one embodiment, the independent components are obtained by higher-order decorrelation of the principal components, and where the higher-order decorrelation of the principal components is achieved by minimizing a function of the higher-order cross-correlation of the data or equivalently by maximizing a function of the higher-order cumulants of the plurality of mixture signals. Since the skew of the time-derivative of the pulse signal is generally much greater in magnitude than that of interference, performance of the ICA may be enhanced by using a "contrast" function that was derived from the third-order cumulants of the derivatives of the signals.

In an aspect of the method of the present invention directed towards a pulse oximeter measuring signals at multiple wavelengths, a first independent component corresponds with a plethysmographic signal, a second independent component corresponds with the interference sources, and sat may be determined from a ratio of mixing coefficients from the mixing matrix. In pulse oximetry, the technique provides the advantage of extracting the plethysmographic signal in the presence of large motion interference and especially without requiring prior knowledge of saturation or pulse rate.

For a further understanding of the nature and advantages of the invention, reference should be made to the following description taken in conjunction with the accompanying drawings.

DETAILED DESCRIPTION OF THE INVENTION

The present invention is directed towards the application of Blind Source Separation (BSS), specifically Independent Component Analysis (ICA) to pulse oximetry. ICA refers to any one of several methods for separating unknown source signals from a set of "mixture" signals, which are linear combinations of the source signals. The ICA method as embodied by the present invention, uses estimates of the second- and higher-order joint statistics of the mixture signals and separates the sources by seeking to minimize the mutual information of the outputs of separation. In pulse oximetry, the signals measured at different wavelengths represent the mixture signals, while the plethysmographic signal, motion artifact, respiratory artifact and instrumental and environmental noise represent the source components.

In one embodiment, the BSS is carried out by a two-step method including an ICA. In the first step, the method uses Principal Component Analysis (PCA) as a preprocessing step, and the Principal Components are then used to derive sat and Independent Components, where the Independent Components are determined in the second step. Before describing the BSS methods of the present invention an example of a pulse oximeter, which may be configured to practice the method of the present invention is described below.

Figure 1:
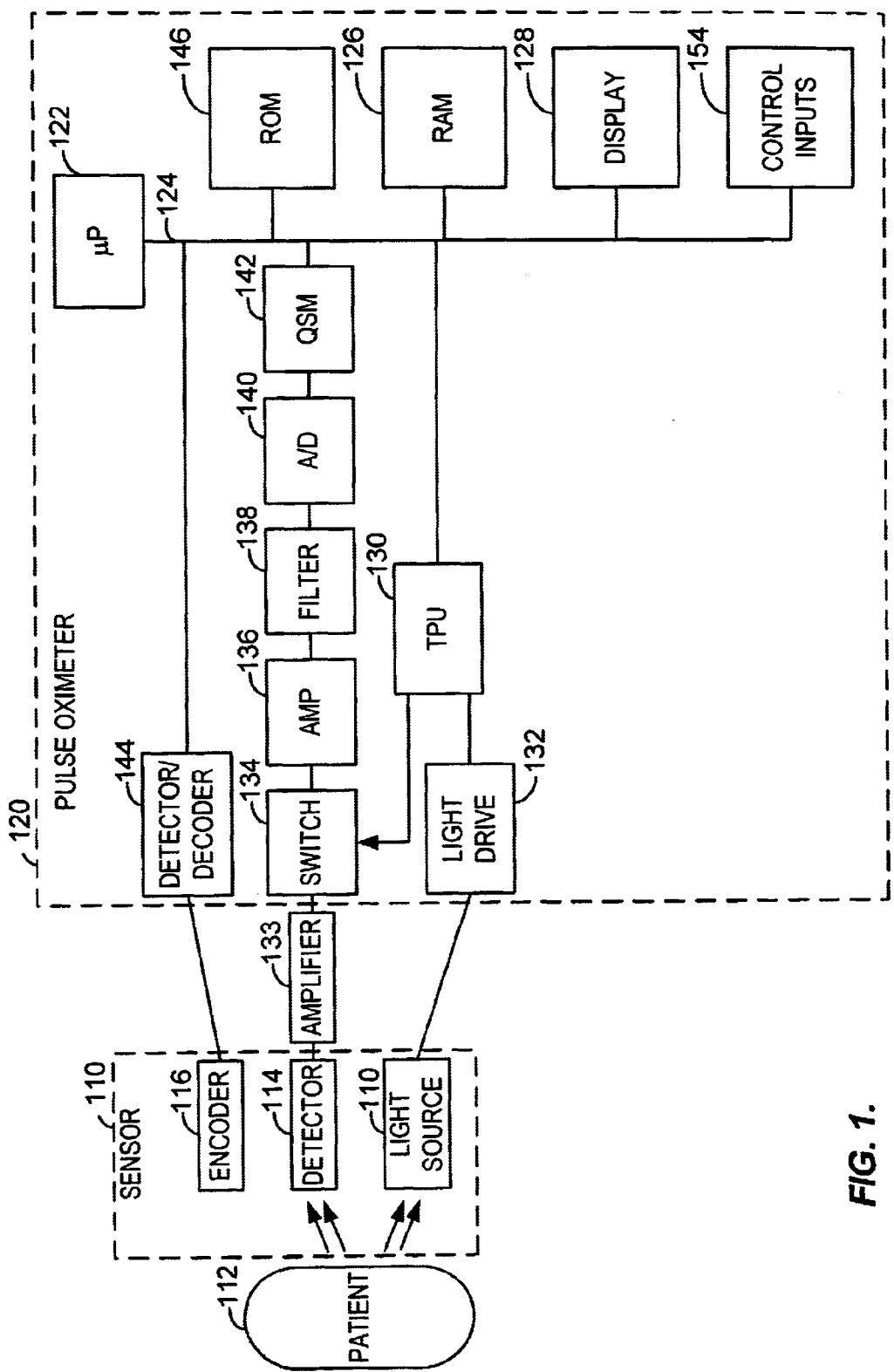
FIG. 1 is a block diagram of an exemplary pulse oximeter.

FIG. 1 is a block diagram of one embodiment of a pulse oximeter implementing the present invention. Light from light source 110 passes into patient tissue 112, and is scattered and detected by photodetector 114. A sensor 100 containing the light source and photodetector may also contain an encoder 116 which provides signals indicative of the wavelength of light source 110 to allow the oximeter to select appropriate calibration coefficients for calculating oxygen saturation. Encoder 116 may, for instance, be a resistor.

Sensor 100 is connected to a pulse oximeter 120. The oximeter includes a microprocessor 122 connected to an internal bus 124. Also connected to the bus is a RAM memory 126 and a display 128. A time processing unit (TPU) 130 provides timing control signals to light drive circuitry 132 which controls when light source 110 is illuminated, and if multiple light sources are used, the multiplexed timing for the different light sources. TPU 130 also controls the gating-in of signals from photodetector 114 through an amplifier 133 and a switching circuit 134. These signals are sampled at the proper time, depending upon which of multiple light sources is illuminated, if multiple light sources are used. The received signal is passed through an amplifier 136, a low pass filter 138, and an analog-to-digital converter 140. The digital data is then stored in a queued serial module (QSM) 142, for later downloading to RAM 126 as QSM 142 fills up. In one embodiment, there may be multiple parallel paths of separate amplifier filter and A/D converters for multiple light wavelengths or spectrums received.

Based on the value of the received signals corresponding to the light received by photodetector 114, microprocessor 122 will calculate the oxygen saturation using various algorithms. These algorithms require coefficients, which may be empirically determined, corresponding to, for example, the wavelengths of light used. These are stored in a ROM 146. The particular set of coefficients chosen for any pair of wavelength spectrums is determined by the value indicated by encoder 116 corresponding to a particular light source in a particular sensor 100. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 154. Control inputs 154 may be, for instance, a switch on the pulse oximeter, a keyboard, or a port providing instructions from a remote host computer. Furthermore any number of methods or algorithms may be used to determine a patient's pulse rate, oxygen saturation or any other desired physiological parameter. One such method, namely Blind Source Separation, is described below.

Blind Source Separation refers to the separation of signals given only linear combinations of those signals, such that:

$$x(t) = A\ s(t)$$

where x(t) is a matrix of a set of observed signals (mixed signals), $x_1(t) \ldots x_n(t)$, A is an unknown mixing matrix, and s(t) is a set of source signals $s_1(t) \ldots s_m(t)$, assumed to be statistically independent, i.e.

$$p(s) = p(s_1, \ldots, s_m) = \prod_{i=1}^{m} p_i(s_i)$$

where p(s) is the probability distribution function of s.

As described above, in pulse oximetry, the mixture signals correspond with signals obtained by a pulse oximeter sensor, which include both the desired signal and the undesired noise components. In one embodiment of the method of the present invention, the mixture signals are first preprocessed using PCA to transform the mixture signal to principal components. To more fully separate the signal and the noise, the data are further processed: in mathematical terms, the data are rotated. In other words, the ICA processing includes a combination of PCA and rotation.

A criterion for determining the degree of signal-noise separation is statistical independence, as described above. However, since the probability distributions are not known, the challenge of an ICA algorithm becomes the measurement of statistical independence. A measure of statistical independence is the degree of mutual information, such that by minimizing the degree of mutual information between sets of data, independent components can be determined. Algorithms determining the mutual information are generally too complicated for a direct solution of its (i.e. mutual information) minimum, and thus they lend themselves best to iterative methods. For example, one possible approach would be to search for coefficients of the mixing matrix A that would lead to statistical independence (by minimizing the data set's mutual information). One could heuristically sweep through a large range of angles about which to rotate the principal components, which would yield an independent set of data, but this approach would be excessively time-consuming.

Thus the inventor of the present invention proposes separating the data by performing higher-order decorrelation of the data, or by removing the higher-order correlation of the data obtained from the mixture signals. Thus, the BSS-based method of the present invention: (1) uses PCA to find uncorrelated components, and (2) separates the data by removing higher-order correlation to find the independent components corresponding with the desired signal source(s) and the undesired noise sources. And as used herein, higher-order correlations are higher than second-order correlations, such as third-order and fourth-order cross-correlations. In one embodiment, independence is approximated by minimizing the sum of the squares of the third-order correlations $r_{xxy}$ and $r_{xyy}$, e.g., $$r_{XXY} = \sum_i x_i^2 y_i \text{ and } r_{XYY} = \sum_i x_i y_i^2$$

[where x and y have zero mean]

Alternately, independence is approximated by minimizing the sum of the squares of the fourth-order cross-cumulants.

In certain embodiments of the present invention, separation is achieved by maximizing the sum of the squares of the higher-order cumulants, which is equivalent to minimizing the sum of the squares of the higher-order cross-cumulants. In these and other embodiments, the second-order decorrelation and higher-order decorrelation may be effected simultaneously through an iterative, adaptive process.

The advantage of achieving separation by higher-order decorrelation is that it enables direct formulas and simple algorithms for the separation of data into its independent components.

Figure 2:
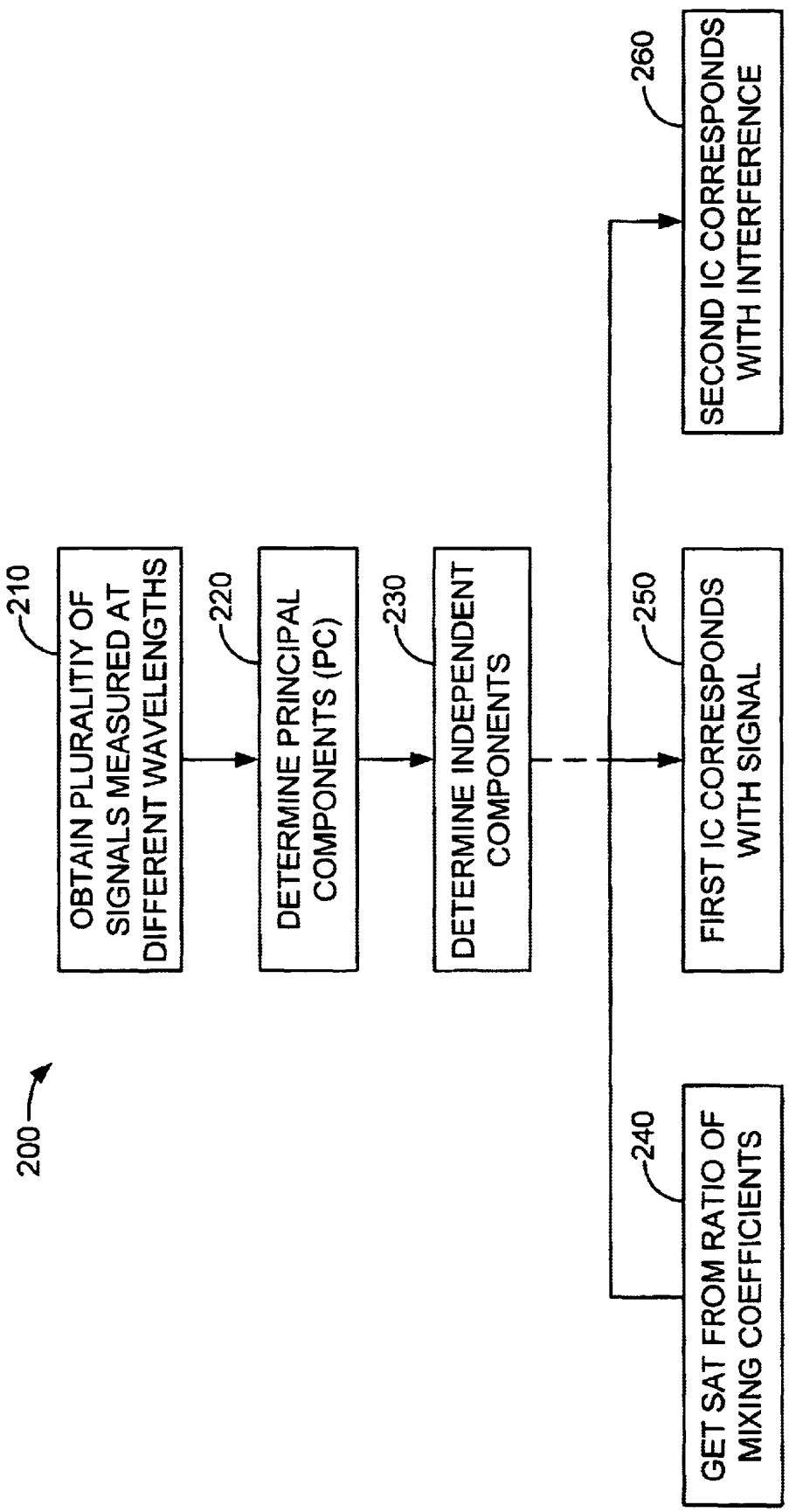
FIG. 2 is a flow chart of an embodiment of the method of the present invention.
Figure 3:
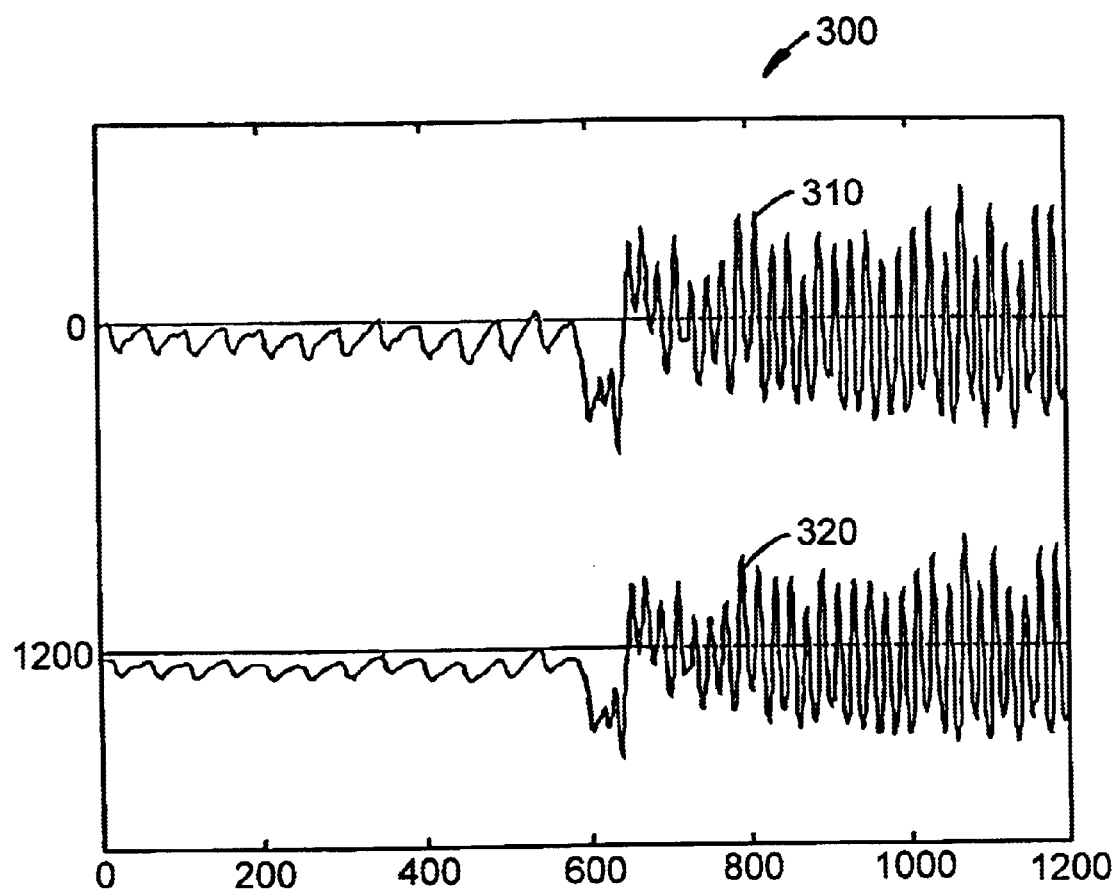
FIG. 3 is a graph showing a typical pulse oximetry signals at two wavelengths.

FIG. 2 is a flow chart 200 of an embodiment the method of the present invention as applied to signals obtained by a pulse oximeter sensor. First, (step 210) a plurality of signals measured at various wavelengths are obtained by a pulse oximeter sensor. In a typical pulse oximeter, emitting optical energy at two wavelengths, the photocurrent generated by the photo-detector is conditioned and processed to determine the modulation ratios of the red and infrared signals. The example of a two-wavelength pulse oximeter is for illustration purposes only, and is not meant to limit the scope of the present invention. The detected photocurrents include the mixture signals, where the mixture signals include the plethysmographic signal, motion artifact, respiratory artifact and instrument noise. An example plot of the measured photocurrent is shown on FIG. 3. FIG. 3 shows a plot 300 of the photocurrent vs. time for measurements obtained at 595 nm (310) and at 665 nm (320). As can be seen from this figure (FIG. 3), both signals (310 and 320) show a low amplitude section and a high amplitude section, where the high amplitude section corresponds to the signals measured while the sensor is moving.

Figure 4:
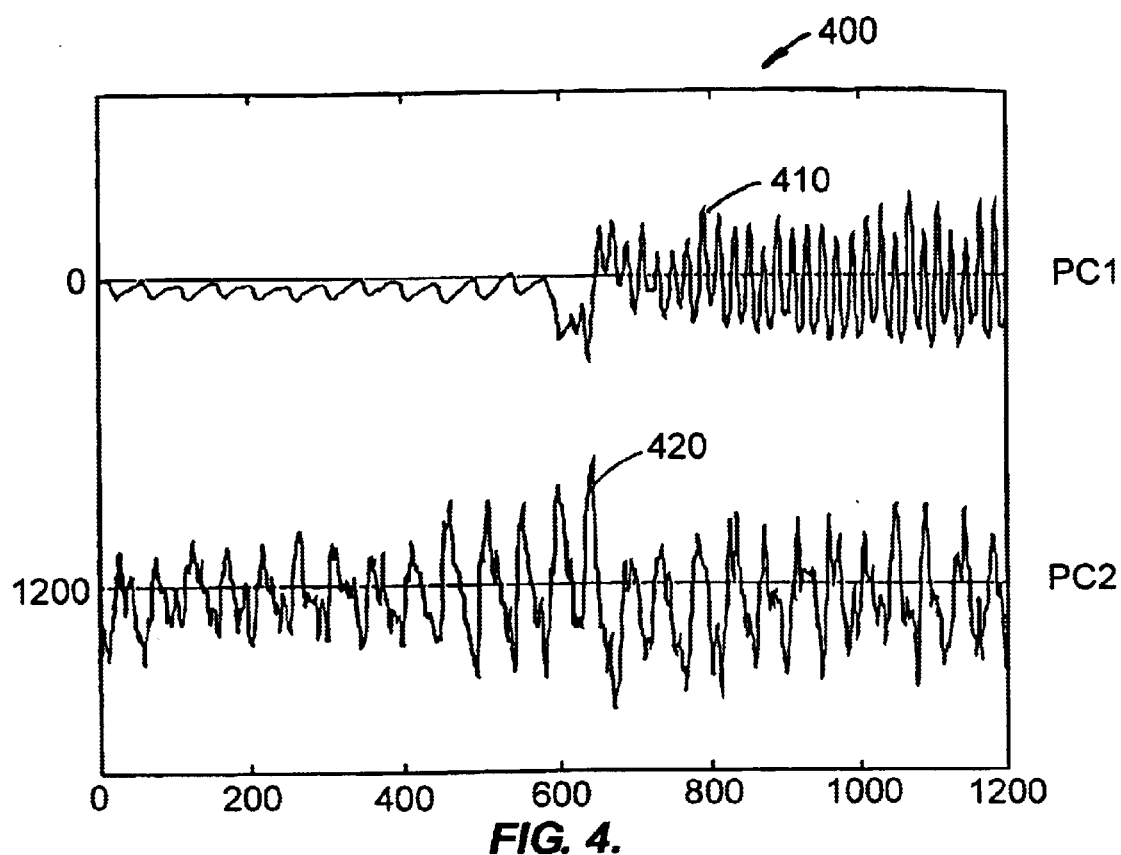
FIG. 4 is a graph showing the typical pulse oximetry signals at two wavelengths after PCA processing.

Next, (step 220) the mixture signals are processed using PCA analysis to obtain two principal components. Here, the PCA processing results in the determination of two principal components, since the original mixture signals were obtained at two different wavelengths. Embodiments of the present invention are not limited to two mixture signals or two principal components. The embodiments of the present invention are directed to the decomposition of a matrix of a set of observed signals (mixed signals) into a set of source signals and a mixing matrix, as set forth above. However, describing more than two dimensions and visualizing more dimensions is at best difficult to visualize, hence the description provided herein is kept to a two-dimensional one. In one embodiment, the Singular Value Decomposition algorithm is used to obtain the principal components. In one alternate embodiment, the data are multiplied by the inverse of the square root of the covariance matrix. In another embodiment directed to a two wavelengths approach, for each possible pair of wavelengths, the data are rotated by the angle of the best linear fit between those two signals. FIG. 4 shows a plot 400 of the two principal components. As can be seen from this figure (FIG. 4), the first principal component 410 corresponds more with the noise due to the subject's motion, since it has a low amplitude portion, which is followed by a high amplitude portion. FIG. 4 also shows that the second principal component 420 corresponds less with the noise due to the subject movement, since it does not show a distinct high amplitude portion.

Figure 6:
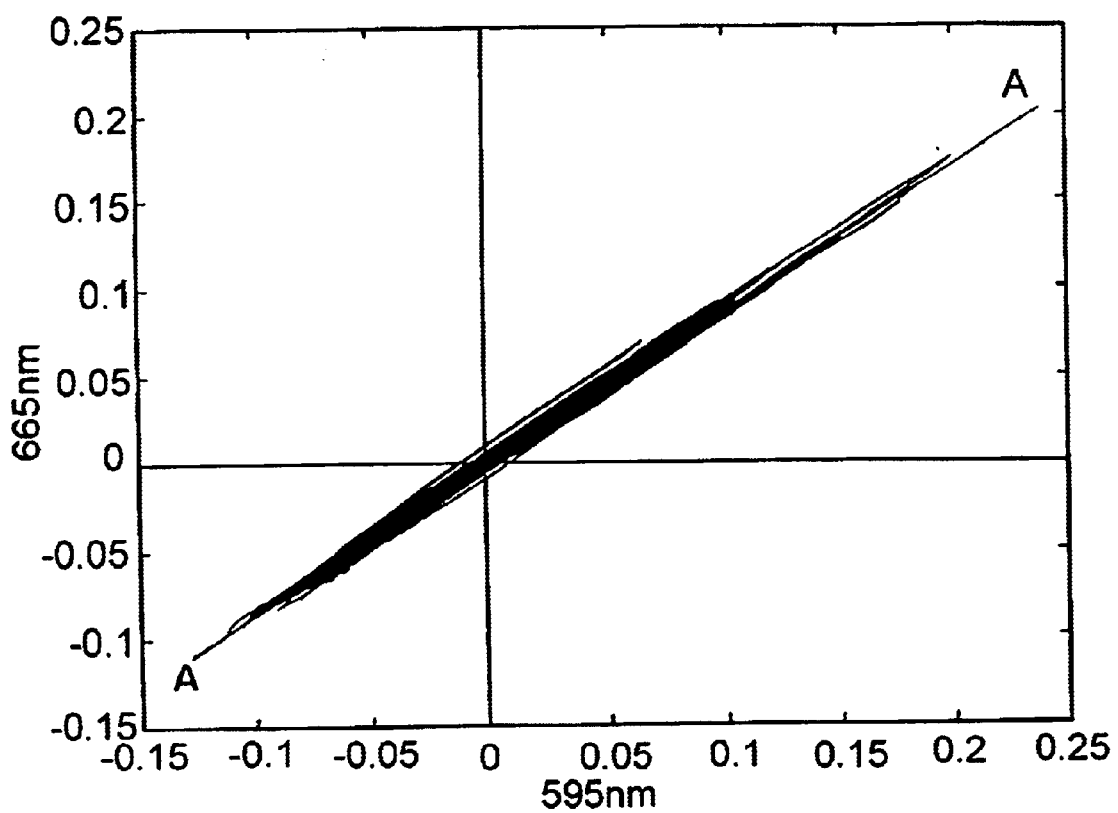
FIG. 6 is a graph of signals of FIG. 3 plotted against one another.
Figure 7:
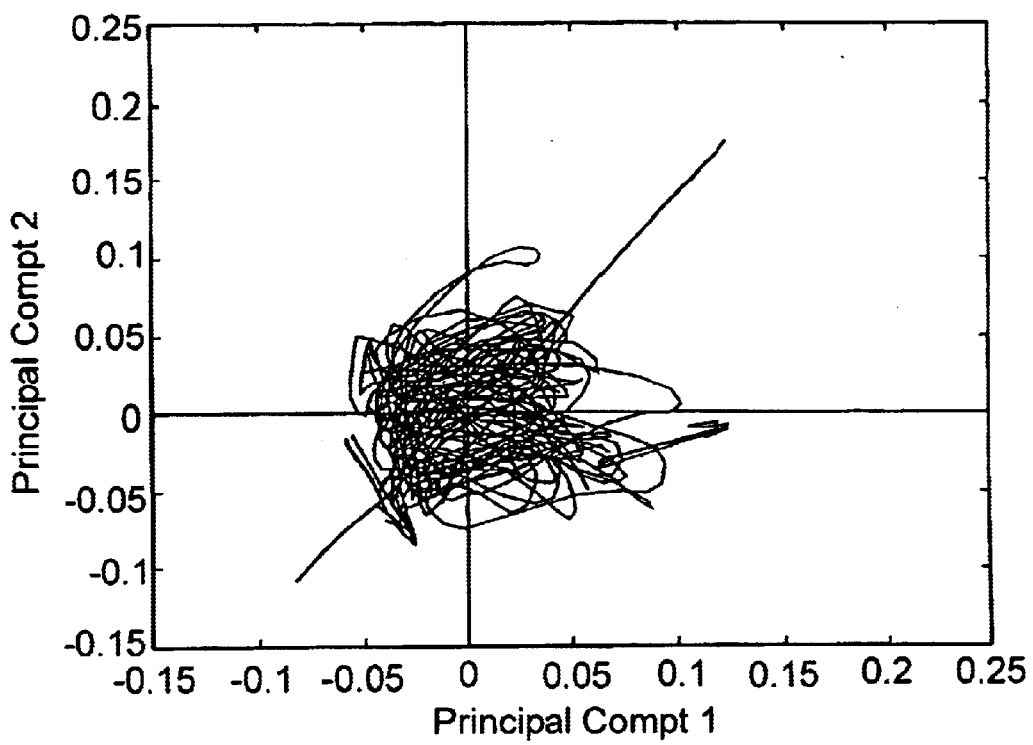
FIG. 7 is a graph of the principal components of FIG. 3 plotted against one another.

Furthermore, a comparison of FIGS. 6 and 7 shows that while the original mixture signals are not decorrelated, the principal components are decorrelated. FIG. 6 shows a graph of the photocurrent at 655 nm vs. the photocurrent at 595 nm. As can be seen from this figure (FIG. 6), there is a wealth of mutual information between the two photocurrents, since the data from the two photocurrents appear to be aligned along the positively sloping diagonal line A—A. FIG. 7 shows a plot of principal component 2 vs. principal component 1. A review of this figure (FIG. 7) shows that the principal components are decorrelated, since there is no significant linear fit to the data in these coordinates.

In an alternate embodiment, before the processing according to step 220, the time derivatives of the signals are obtained. For pulse oximetry, the third-order correlations of the pulse signals are often enhanced by taking the time derivative of the signals before performing PCA/ICA analyses.

Figure 5:
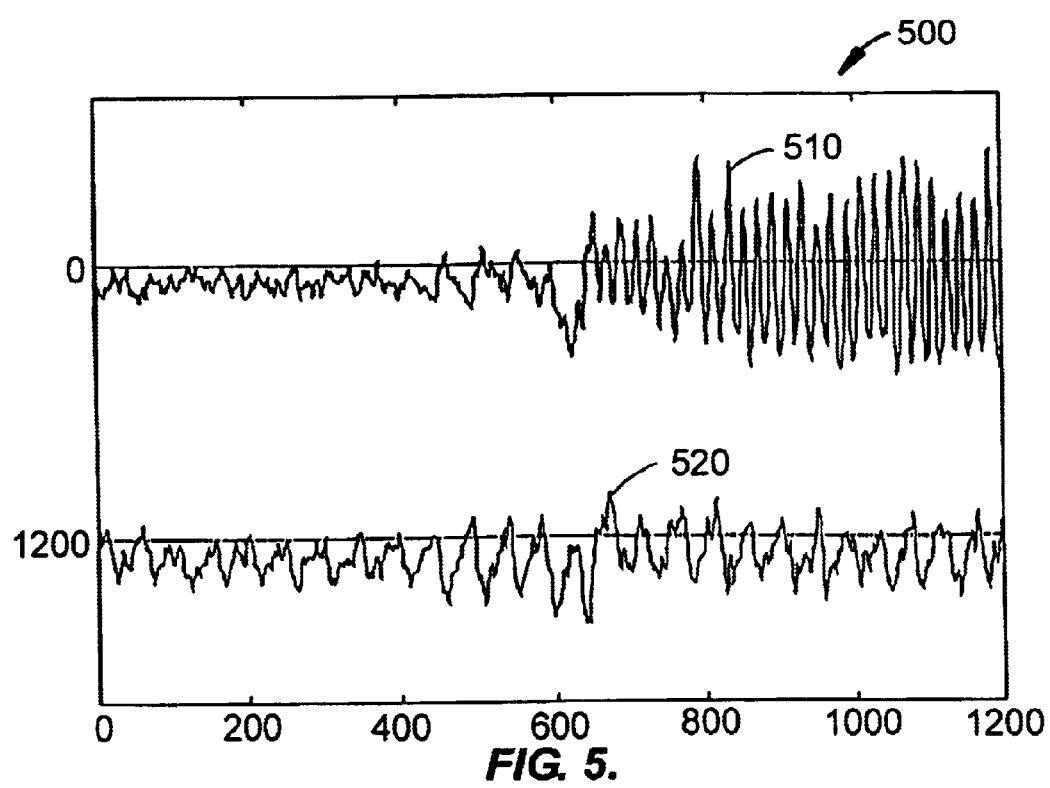
FIG. 5 is a graph showing a typical pulse oximetry signals at two wavelengths after ICA processing.
Figure 8:
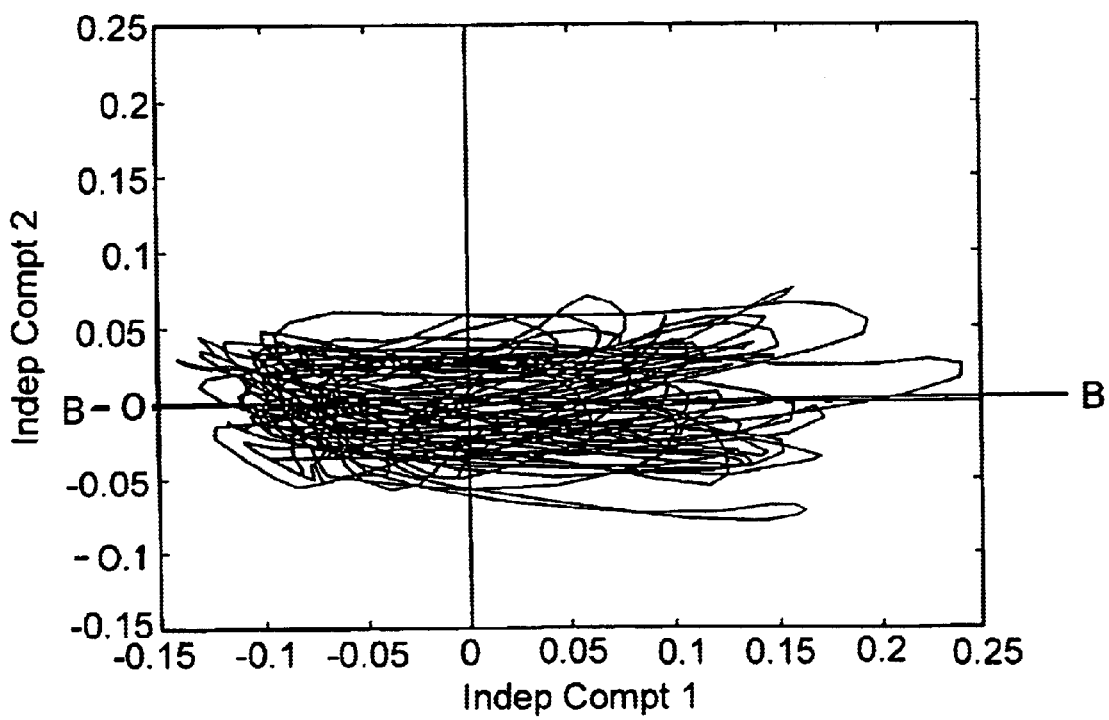
FIG. 8 is a graph of the independent components of FIG. 3 plotted against one another.

Having decorrelated the data, the principal components are further processed by ICA processing to determine the independent components describing the photocurrent data (step 230). As described above, the principal components are processed to obtain a plurality of independent components, wherein a matrix of the plurality of signals corresponds with a matrix product of a matrix of the plurality of independent components and a matrix of mixing coefficients. In one embodiment, the independent components are determined by decorrelating the data by maximizing the sum of squares of the data set's higher-order cumulants. Since the skew of the time-derivative of the pulse signal is generally much greater in magnitude than that of interference, the ICA performance is enhanced by using a "contrast" function that was derived from the third-order cumulants of the derivatives of the signals. As stated above, a contrast function is any non-linear function which is invariant to permutation and scaling matrices, and attains its minimum value in correspondence of the mutual independence among the output components. In an alternate embodiment, the independent components are determined by minimizing the estimated mutual information. FIG. 5 shows a plot 500 of the two independent components. As can be seen from this figure (FIG. 5), a first independent component 510 corresponds more with the noise due to the subject's motion, since it has a low amplitude portion, which is followed by a high amplitude portion. FIG. 5 also shows that a second principal component 520 apparently corresponds to a pulse component. Furthermore, FIG. 8 shows a plot of independent component 2 vs. independent component 1. As can be seen from this figure (FIG. 8), the plot of independent component 2 vs. independent component 1 lies along the horizontal line at (independent component=0) B—B, showing that the data sets have a minimal amount of mutual information, and thus can be approximated as independent data sets.

The decomposed data set of two independent components is further processed as follows. In one embodiment, sat is obtained from a ratio of mixing coefficients (step 240). In an alternate embodiment, one of the independent components is further processed to obtain the plethysmographic signal (step 250), and the other independent signal is recognized as a measure of the interference signal (step 260).

Alternately, instead of, or in addition to taking signals that are measured at different wavelengths (step 210), signals are also obtained that are additions of signals from different times, thus an alternate embodiment of the present invention starts by processing signals obtained from mixing signals in time.

In pulse oximetry, embodiments of the present invention have the advantage of extracting the plethysmographic signal in the presence of large motion interference and especially without requiring prior knowledge of saturation or pulse rate. Additionally, the present method is extendible to measurement of other physiological variables, such as pulse rate, blood pressure, temperature, or any other physiological variable measurable by non-invasive measurement of photocurrent provided an optical-based sensor.

Accordingly, as will be understood by those of skill in the art, the present invention which is related to blind source separation of pulse oximetry signals, may be embodied in other specific forms without departing from the essential characteristics thereof. Accordingly, the foregoing disclosure is intended to be illustrative, but not limiting, of the scope of the invention, which is set forth in the following claims.

What is claimed is:

1. A method for measuring a physiological parameter, comprising:

measuring a plurality of signals, wherein each of said signals comprises a source component corresponding to said physiological parameter and an interference component;

processing said plurality of signals to obtain a plurality of principal components;

processing said plurality of principal components to obtain a plurality of independent components, wherein a matrix of said plurality of signals corresponds to a matrix product of a matrix of said plurality of independent components and a matrix of mixing coefficients; and extracting a first measure of said physiological parameter corresponding to said source component from one of said plurality of independent components, wherein said plurality of signals corresponds to sensed optical energies from a plurality of wavelengths.

2. The method of claim 1 wherein said physiological parameter is a function of an oxygen saturation.

3. The method of claim 1 wherein said processing said plurality of signals further comprises obtaining a time derivative of the sensed optical energies from a plurality of wavelengths.

4. The method of claim 1 wherein said interference component comprises signal components caused by motion, respiratory artifact, ambient light, optical scattering and other interference between a tissue location being sensed and a sensor.

5. The method of claim 1 wherein said processing said plurality of signals further comprises decorrelating said plurality of signals by minimizing a cross-correlation of said plurality of signals, to obtain a plurality of decorrelated signals; and normalizing said plurality of decorrelated signals to obtain the plurality of principal components.

6. The method of claim 1 wherein said processing said plurality of signals comprises decorrelating said plurality of signals by singular-value decomposition of said plurality of signals, to obtain the plurality of principal components.

7. The method of claim 1 wherein said processing said plurality of signals comprises decorrelating said plurality of signals by multiplying said plurality of signals the inverse square root of the covariance matrix of said plurality of signals to obtain the plurality of principal components.

8. The method of claim 1 wherein said processing of said plurality of principal components comprises higher-order decorrelation of said plurality of principal components.

9. The method of claim 1 wherein said processing said plurality of principal components comprises maximizing a function of the higher-order cumulants of a mixture of said plurality of signals, thus separating said source component from said interference component.

10. The method of claim 9 wherein said higher-order cumulant is cumulant having order greater than two.

11. The method of claim 9 wherein said higher-order cumulant is a third-order cumulant of said plurality of signals.

12. The method of claim 9 wherein said higher-order cumulant is a fourth-order cumulant of said plurality of signals.

13. The method of claim 1 further comprising obtaining a ratio of mixing coefficients from said matrix of mixing coefficients, wherein said ratio corresponds to a ratio of modulation ratios of red to infrared signals, wherein said plurality of signals comprise modulated optical signals in the red and infrared ranges.

14. The method of claim 13 further comprising extracting a second measure of said physiological parameter from said ratio, wherein said second measure of said physiological parameter corresponds to an oxygen saturation.

15. The method of claim 1 further comprising extracting said interference component from another one of said plurality of independent components.

16. A method for measuring a physiological parameter, comprising:

measuring a plurality of signals, wherein each of said signals comprises a source component corresponding to said physiological parameter and an interference component;

processing said plurality of signals to obtain a plurality of principal components;

processing said plurality of principal components to obtain a plurality of independent components, wherein a matrix of said plurality of signals corresponds to a matrix product of a matrix of said plurality of independent components and a matrix of mixing coefficients; and extracting a first measure of said physiological parameter corresponding to said source component from one of said plurality of independent components, wherein said physiological parameter is a function of a pulse rate.

17. A method for measuring a physiological parameter, comprising:

measuring a plurality of signals, wherein each of said signals comprises a source component corresponding to said physiological parameter and an interference component;

processing said plurality of signals to obtain a plurality of principal components;

processing said plurality of principal components to obtain a plurality of independent components, wherein a matrix of said plurality of signals corresponds to a matrix product of a matrix of said plurality of independent components and a matrix of mixing coefficients; and extracting a first measure of said physiological parameter corresponding to said source component from one of said plurality of independent components, wherein said plurality of signals corresponds to sensed optical energies from a plurality of wavelengths from different times.

18. A method for measuring a physiological parameter, comprising:

measuring a plurality of signals, wherein each of said signals comprises a source component corresponding to said physiological parameter and an interference component;

processing said plurality of signals to obtain a plurality of principal components;

processing said plurality of principal components to obtain a plurality of independent components, wherein a matrix of said plurality of signals corresponds to a matrix product of a matrix of said plurality of independent components and a matrix of mixing coefficients; and extracting a first measure of said physiological parameter corresponding to said source component from one of said plurality of independent components, wherein said first measure of a physiological parameter corresponds to a pulse rate.

19. A pulse oximeter, comprising:

a sensor configured for measuring a plurality of signals, wherein each of said signals comprises a source component corresponding to said physiological parameter and an interference component;

a computer useable medium having computer readable code embodied therein for measuring a physiological parameter, said computer readable code configured to execute functions comprising:

processing said plurality of signals to obtain a plurality of principal components;

processing said plurality of principle components to obtain a plurality of independent components, wherein a matrix of said plurality of signals corresponds to a matrix product of a matrix of said plurality of independent components and a matrix of mixing coefficients; and extracting a first measure of said physiological parameter corresponding to said source component from one of said plurality of independent components, wherein said physiological parameter is a pulse rate.

20. A pulse oximeter, comprising:

a sensor configured for measuring a plurality of signals, wherein each of said signals comprises a source component corresponding to said physiological parameter and an interference component;

a computer useable medium having computer readable code embodied therein for measuring a physiological parameter, said computer readable code configured to execute functions comprising:

processing said plurality of signals to obtain a plurality of principal components;

processing said plurality of principle components to obtain a plurality of independent components, wherein a matrix of said plurality of signals corresponds to a matrix product of a matrix of said plurality of independent components and a matrix of mixing coefficients; and extracting a first measure of said physiological parameter corresponding to said source component from one of said plurality of independent components, wherein said plurality of signals corresponds to sensed optical energies from a plurality of wavelengths.

21. The pulse oximeter of claim 20 wherein said physiological parameter is an oxygen saturation.

22. The pulse oximeter of claim 20 wherein said plurality of signals corresponds to the time derivative of the sensed optical energies from a plurality of wavelengths.

23. The pulse oximeter of claim 20 wherein said interference component comprises signal components caused by motion, respiratory artifact, ambient light, optical scattering and other interference between a tissue location being sense and a sensor.

24. The pulse oximeter of claim 20 wherein said processing said plurality of signals comprises decorrelating said plurality of signals by minimizing a cross-correlation of said plurality of signals, to obtain a plurality of decorrelated signals; and normalizing said plurality of decorrelated signals to obtain the plurality of principal components.

25. The pulse oximeter of claim 20 wherein said processing said plurality of signals comprises decorrelating said plurality of signals by singular-value decomposition of said plurality of signals, to obtain the plurality of principal components.

26. The pulse oximeter of claim 20 wherein said processing said plurality of signals comprises decorrelating said plurality of signals by multiplying said plurality of signals by the inverse square root of the covariance matrix of said plurality of signals to obtain the plurality of principal components.

27. The pulse oximeter of claim 20 wherein said processing of said plurality of principal components comprises higher-order decorrelation of said plurality of principal components.

28. The pulse oximeter of claim 20 wherein said processing said plurality of principal components comprises maximizing a function of the higher-order cumulants of a mixture of said plurality of signals, thus separating said source component from said interference component.

29. The pulse oximeter of claim 28, wherein said higher-order cumulant is cumulant having order greater than two.

30. The pulse oximeter of claim 28, wherein said higher-order order cumulant is a third-order cumulant of said plurality of signals.

31. The pulse oximeter of claim 28 wherein said higher-order order cumulant is a fourth-order cumulant of said plurality of signals.

32. The pulse oximeter of claim 20 wherein said processing said plurality of principal components comprises successive transformations to simultaneously minimize second- and higher-order correlations among the outputs of the transformations.

33. The pulse oximeter of claim 20 wherein said processing said plurality of principal components comprises successive rotations to minimize estimated mutual information among outputs of the invention.

34. The pulse oximeter of claim 20 further comprising obtaining a ratio of mixing coefficients from said matrix of mixing coefficients, wherein said ratio corresponds to a ratio of modulation ratios of red to infrared signals.

35. The pulse oximeter of claim 34 further comprising extracting a second measure of said physiological parameter from said ratio, wherein said second measure of said physiological parameter corresponds to an oxygen saturation.

36. The pulse oximeter of claim 20 wherein said first measure of a physiological parameter corresponds a pulse rate.

37. The pulse oximeter of claim 20 further comprising extracting said interference component from another one of said plurality of independent components.

38. A pulse oximeter, comprising:

a sensor configured for measuring a plurality of signals, wherein each of said signals comprises a source component corresponding to said physiological parameter and an interference component;

a computer useable medium having computer readable code embodied therein for measuring a physiological parameter, said computer readable code configured to execute functions comprising:

processing said plurality of signals to obtain a plurality of principal components;

processing said plurality of principle components to obtain a plurality of independent components, wherein a matrix of said plurality of signals corresponds to a matrix product of a matrix of said plurality of independent components and a matrix of mixing coefficients; and extracting a first measure of said physiological parameter corresponding to said source component from one of said plurality of independent components, wherein said plurality of signals corresponds to sensed optical energies from a plurality of wavelengths from different times.

* * * * *